(12) United States Patent
Rosenberg et al.

(10) Patent No.: US 6,562,620 B2
(45) Date of Patent: May 13, 2003

(54) MEDIUM TO PROMOTE ISLET CELL SURVIVAL

(75) Inventors: Lawrence Rosenberg, Montreal (CA); Dusica Maysinger, Montreal (CA)

(73) Assignee: McGill University, Montreal (CA)

( * ) Notice: Subject to any disclaimer, the term of this patent is extended or adjusted under 35 U.S.C. 154(b) by 39 days.

(21) Appl. No.: 10/138,517

(22) Filed: May 6, 2002

(65) Prior Publication Data

US 2002/0172665 A1 Nov. 21, 2002

Related U.S. Application Data

(63) Continuation-in-part of application No. 09/508,822, filed as application No. PCT/CA98/00887 on Sep. 17, 1998, now abandoned.

(30) Foreign Application Priority Data

Sep. 19, 1997 (CA) .............................................. 2216055

(51) Int. Cl.$^7$ .................................................... C12N 5/00
(52) U.S. Cl. ........................ 435/406; 435/385; 435/387; 435/403; 435/405
(58) Field of Search ................................. 435/385, 387, 435/403, 405, 406; 424/93.7

(56) References Cited

FOREIGN PATENT DOCUMENTS

| EP | 0184162 A2 | * | 11/1985 |
| WO | WO 97/16536 A1 | * | 5/1997 |

\* cited by examiner

*Primary Examiner*—Leon B. Lankford, Jr.
(74) *Attorney, Agent, or Firm*—Crowell & Moring LLP (57) ABSTRACT

The present invention relates to a medium for promoting the survival of islet cells, which comprises one or more growth factors in combination with FK506 in amounts having an anti-apoptotic effect on islet cells in a physiologically acceptable culture medium.

27 Claims, 12 Drawing Sheets

MEDIUM TO PROMOTE ISLET CELL SURVIVAL

RELATED APPLICATIONS

This application is a continuation-in-part of application Ser. No. 9/508,822 filed on Sep. 12, 2000 now abandoned, still pending and is a national phase entry in the United States of PCT/CA98/00887 filed on Sep. 17, 1998.

BACKGROUND OF THE INVENTION (a) Field of the Invention

The invention relates to a culture medium which promote islet cells survival, which may be transplanted to reverse hyperglycemia.

(b) Description of Prior Art

Adequate numbers of isogeneic islets transplanted into a reliable implantation site can only reverse the metabolic abnormalities in diabetic recipients in the short term. In those that were normoglycemic post-transplant, hyperglycemia recurred within 3–12 months. The return of the diabetic state that occurs with time has been attributed either to the ectopic location of the islets, to a disruption of the entero-insular axis, or to the transplantation of an inadequate islet cell mass.

Studies of the long term natural history of the islet transplant, that examine parameters other than graft function, are few in number. Only one report was found in which an attempt was specifically made to study graft morphology (Alejandro R. et al., *J. Clin. Invest.*, 1986, 78:1339). In that study, purified islets were transplanted into the canine liver via the portal vein. During prolonged follow-up, delayed failures of graft function occurred. Unfortunately, the graft was only examined at the end of the study, and not over time as function declined. Delayed graft failures have also been confirmed by other investigators for dogs and primates. Most failures are presumed to be the result of rejection despite appropriate immunosuppression.

Because of these failures, there is currently much enthusiasm for the immunoisolation of islets, which could eliminate the need for immunosuppression. The reasons are compelling., Immunosuppression is harmful to the recipient, and may impair islet function and possibly cell survival. Unfortunately, micro-encapsulated islets injected into the peritoneal cavity of the dog fail within 6 months (Soon-Shiong P. et al., *Transplantation*, 1992, 54:769), and islets placed into a vascularized biohybrid pancreas also fail, but at about one year (Lanza RP et al., *Diabetes*, 1992, 41:1503). Histological evaluation indicates a substantial loss of islet mass in these devices. No reasons have been advanced for these changes.

Only whole pancreas transplantation is capable of permanently reversing the diabetic state and preventing the secondary complications of diabetes. This suggests that there is a fundamental biological difference between grafts of whole pancreas and those of purified islets.

It is perhaps significant that the major emphasis in islet transplantation has been the enhancement of the purity of the islet preparation to promote engraftment and reduce immunogenicity. After more than 20 years of concerted research and more than 200 attempts at human islet transplantation, the achievement of insulin independence remains elusive. Contamination of the islet preparation by non-endocrine cells does not impair function or engraftment, nor enhance immunogenicity. In a canine model, pancreatic tissue fragments autotransplanted into the spleen appeared to survive better than islets refluxed into the liver (Kretemom NM and Warnock GL, *Transplantation*, 1990, 49, 679). The survival advantage was attributed to the specific site, but pancreatic fragments may actually have an inherent survival advantage compared to purified islets. In people, insulin-independence has been obtained after intraportal injection of unpurified autologous islets. Fewer impure islets were more successful than many more purified ones. A similar experience was repeated with allotransplants, with unpurified islets from a single human pancreas successfully reversing hyperglycemia (Gores PF et al., *Lancet*, 1993, 341:19). From these and other reports, it is apparent that unpurified islets from one pancreas may survive as well as pure islets prepared from multiple donors.

To date, the only known roles of apoptosis, or programmed cell death, in the regulation of islet cell mass are in the involution of β cell mass after pregnancy and perhaps in remodeling during development as recently suggested by Finegood (Finegood OT et al., *Diabetes*, 1995, 44:249). These situations, however, are physiologic in nature and it remains to be determined under what unusual circumstances islets may also be induced to undergo apoptotic cell death. The recent report of a selective decrease in β cell mass following transplantation of human islets into diabetic nude mice is therefore of considerable interest. The induction of apoptosis in relation to islet isolation and transplantation has not been reported previously. We have original observations on human islets after isolation. Light microscopic examination of these islets just prior to culture demonstrates that at least 15% of the cells have morphological evidence of apoptosis (pyknotic nuclei). Tissue transglutaminase (TG) expression is a fundamental event in the induction of apoptosis. TG is a calcium-dependent enzyme whose activity is well established in many mammalian tissues, including pancreas. It is involved in the cross-linking of intracellular proteins that precedes the irreversible ultrastructural changes characterizing cells undergoing apoptosis. The appearance of apoptotic bodies parallels an increased expression of TG. Our pilot studies have shown TG activity to be elevated immediately following islet isolation, with continued increase up to at least 1 week. These findings correlated with data from a cell death ELISA that detects histone-associated DNA fragments, another characteristic of the apoptotic process (Paraskevas S. et al., *Transplant Proc.*, 1997, 29:750). These fragments result from the activity of an endonuclease that cleaves DNA at internucleosomal sites. These data form the basis for investigating the role of apoptosis in islet survival after isolation.

It would be highly desirable to be provided with a means to prevent apoptosis of islet cells, thereby allowing transplantation with the successful reversal of hyperglycemia.

SUMMARY OF THE INVENTION

One aim of the present invention is to provide a culture medium which promotes the survival islet cell, which may be transplanted to reverse hyperglycemia.

In accordance with the present invention there is provided a medium for promoting the survival of islet cells, which comprises one or more growth factors in combination with FK506 in amounts having an anti-apoptotic effect on islet cells in a physiologically acceptable culture medium.

In accordance with a preferred embodiment of the present invention, a culture medium, herein referred to as duct-conditioned medium (DCM), is prepared from primary duct cultures that had been passaged twice to remove other cellular elements. DCM was analyzed for known growth factors. The presence of a large amount of IGF-II (34 ng/ml) and a much smaller quantity of NGF (4 ng/ml) were identified.

In accordance with another embodiment of the present invention there is provided a medium for promoting the survival of islet cells comprising, in a physiologically culture medium, IGF-I or IGF-II in combination with NGF in an amount having a synergistic anti-apoptotic effect on islet cells. More preferably, this medium further includes FK-506.

The preferred growth factors include, without limitation, NGF, IGF-II and insulin. Other growth factors include TGFβ, IGF-I and HGF.

The preferred NGF concentration is between about 10 to about 100 ng/ml of medium.

The preferred IGF-II concentration is between about 10 to about 100 ng/ml of medium.

Preferably, the culture medium of the present invention includes an immunosuppressant.

The preferred immunosuppressants are selected from the group consisting of FK506, a peptide having NGF potentiating effect, and therefore possibly a trophic effect on islet cells.

The preferred FK506 concentration is about 1 micromolar.

More preferably, the culture medium of the present invention further includes insulin. The preferred insulin concentration is from about 10 to about 100 ng/ml of medium.

More preferably, the culture medium of the present invention further includes a soluble matrix molecule called fibronectin and type I collagen.

The term "physiologically acceptable culture medium" is intended to mean any commercially available culture medium including, without limitation, CMRL 1066, RAM 1640 and DMEM/F12.

The culture medium of the present invention may also be used to isolate islet cells or to irrigate the site of transplant to promote in situ islet cells survival.

BRIEF DESCRIPTION OF THE DRAWINGS

FIG. 2 illustrates TUNEL staining of porcine islets, (A) islets incubated in the standard medium and (B) islets incubated with insulin;

FIG. 6 illustrates activation and expression of erk-1 and erk-2 in isolated islets in absence or presence of growth factors;

DETAILED DESCRIPTION OF THE INVENTION

Growth factors act in an autocrine and/or paracrine manner to mediate a broad range of cellular responses, including ECM formation, cell proliferation and differentiation. The role of these factors in islet cell survival in the pancreas is relatively unexplored.

Hepatocyte growth factor (HGF) has effects on a wide variety of epithelial cell types, including pancreas, where it has been detected in acinar and islet cells. It has no known role in the adult pancreas. In comparison, Insulin-like growth factors (IGFs) effect cell growth and differentiation in both the fetal and adult pancreas. During induced islet cell neogenesis in the adult hamster, we have found that β cell differentiation from the ductal epithelium was associated with a transient increase in IGF-II expression, recapitulating the fetal environment as characterized by Hill (Rafacloff R et al., *Diabetes*, 1993, 42(suppl.1) :137A). This suggests a direct role for IGF-II in the differentiation process in the adult. Evidence for IGFs as survival factors has also been reported. Similarly, recent findings support a role for Nerve growth factor (NGF) in normal development, morphogenesis and functional maturation of islets. Greater uncertainty surrounds reg, a gene that is over-expressed within pancreatic cells after pancreatitis or resection, and particularly during islet cell regeneration. We and others have found that the reg gene is induced in our model of islet neogenesis. Although it has been hypothesized that reg is an important paracrine factor in the maintenance and growth of β-cells, the true significance of this gene remains to be determined. Transforming Growth Factor (TGF) –α is a mitogen expressed in pancreatic duct and acinar cells, whose role in maintaining cell survival is undefined. TGF-β is also a potent regulator of cell proliferation, but its major activity is to stimulate the synthesis and deposition of various ECM proteins and to increase the expression of integrins. TGF-β expression in vivo may be important in the re-establishment of basement membrane following its loss during islet isolation, and hence in islet cell survival.

Growth factors may also be inhibitory in almost all situations in which apoptosis, or programmed cell death, is positively stimulated. This suggests that regulation of growth factor levels is not only important in the control of cell proliferation but also in maintaining viability of cells susceptible to apoptosis. These data suggest, that for the success of islet transplantation, the activity of survival factors may be fundamental to the long term maintenance of graft function.

The Preferred Islet Survival Medium of the Present Invention

The formulation of the preferred medium of the present invention takes advantage of (1) newly recognized effects of known growth factors on inhibiting the induction of apoptosis in islet cells, (2) the combination of these factors to achieve a synergistic beneficial effect on islet cell survival, and (3) the potentiation of this synergistic effect by the addition of the drug FK506 (ProGraf®, Fujisawa).

The growth factors that have been combined are NGF (nerve growth factor), IGF-I (insulin-like growth factor-1)

and insulin. None has been previously known to play a role in the prevention of apoptosis. Certainly, the role of NGF on islet tissue has only recently been recognized with respect to islet cell differentiation during normal fetal development. Its known trophic effects on cells have been solely in relation to neuronal cells. Similarly, IGF-I is active in islet cell differentiation during fetal development, but a role in apoptosis has never been reported.

FK506 is a macrolide immunosuppressive agent which acts by inhibiting T-cell activation. FK506 is a ligand for the immunophilin FKBP12. The FK506-FKBP12 complex binds several targets, one of which is the calcium calmodulin dependent phosphatase, calcineurin. FK506 has been shown to potentiate the neurotropic effects of NGF. The exact mechanism by which FK506 facilitates NGF activity is still unclear.

We have demonstrated that a CMRL 1066 medium (a conventional islet culture medium) supplemented with the above substances can significantly reduce the amount of apoptotic cell death sustained by insulin-producing β-cells following islet isolation and purification.

The evidence is based on four assays.

First, Western blots demonstrate that the balance between activation of stress-activated protein kinases (SAPK) including JNK1/JNK2 and p38 relative to erk1/erk2, is altered. The former two pathways are known to be associated with the induction of the apoptotic program, while the latter may be protective.

Figure 1:
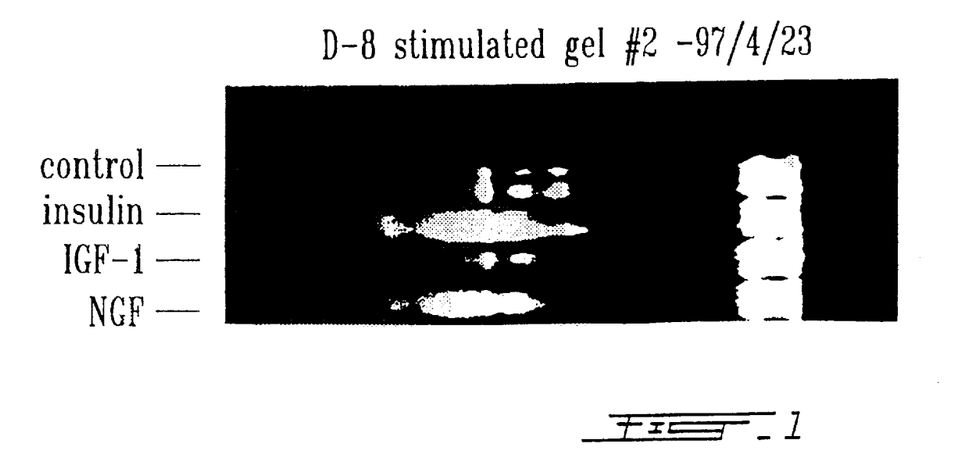
FIG. 1 illustrates an Agarose gel demonstrating DNA laddering in islets incubated in a control medium (control lane), compared to islets incubated with insulin or NGF.

Second, there is a significant reduction on agarose gels of the DNA laddering that is characteristic for the DNA fragmentation that is the outcome of apoptosis (FIG. 1).

Figure 2A:
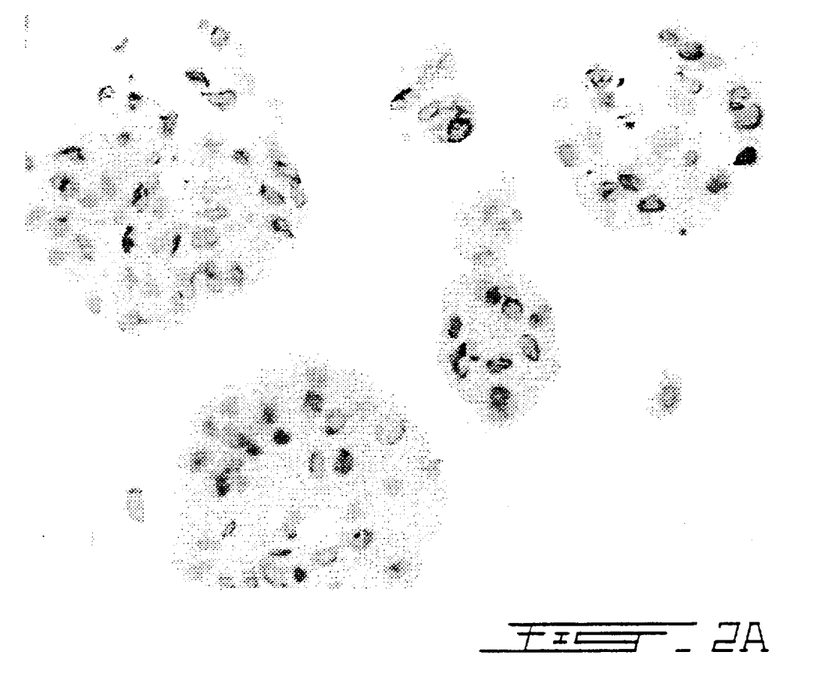
Figure 2B:
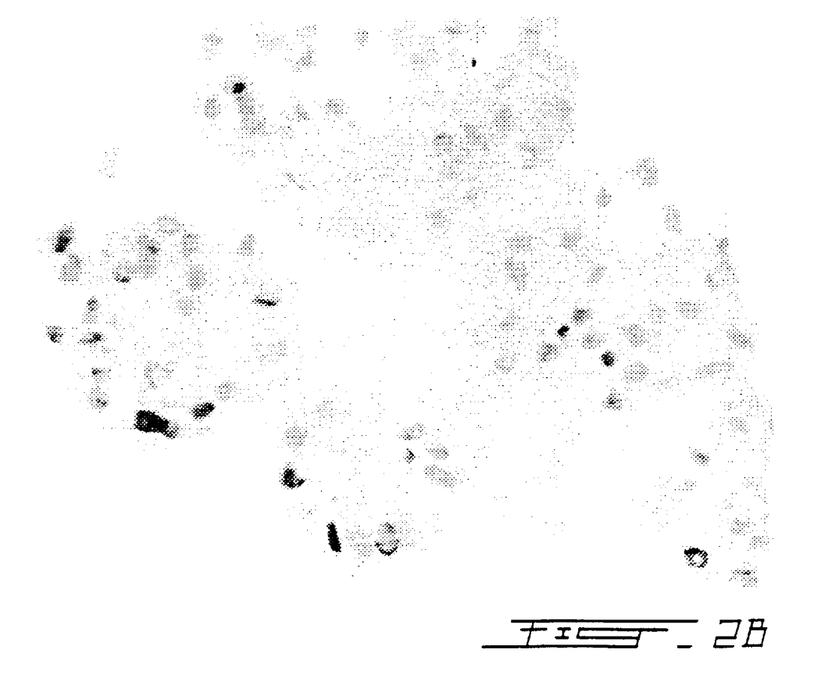

Third, TUNEL staining (another technique to visualize apoptotic events) of actual isolated islets, demonstrates a significant reduction in the number of apoptotic cells (FIG. 2).

Figure 3:
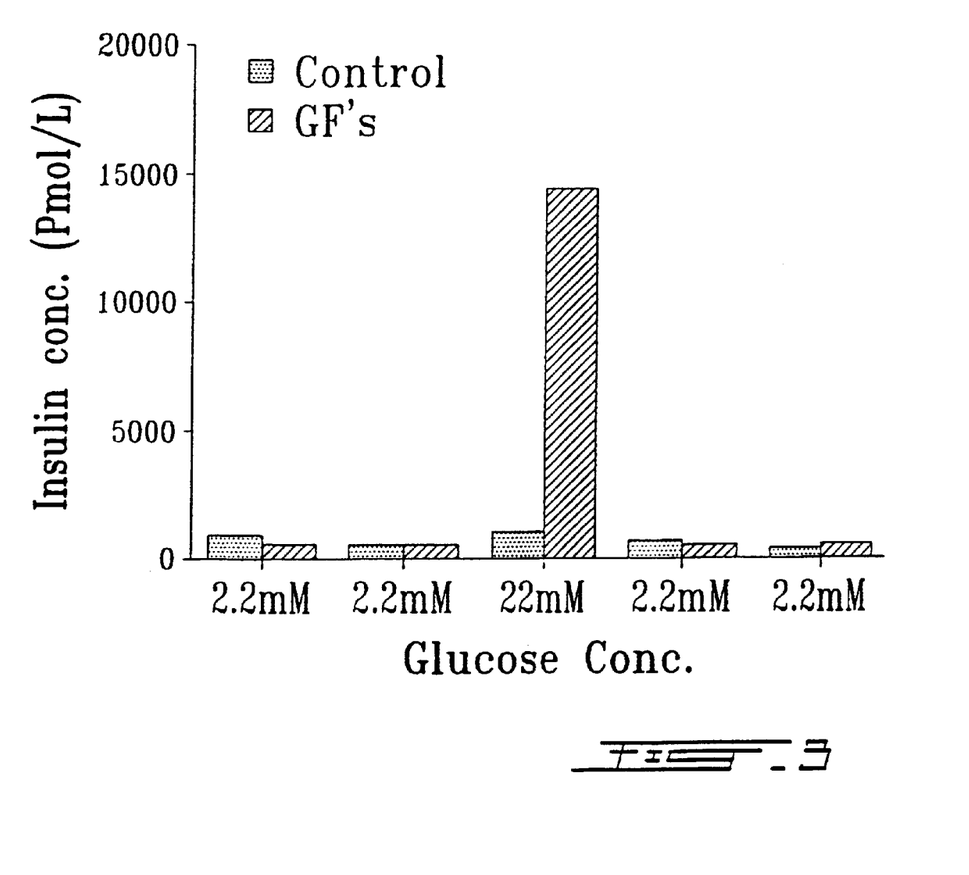
FIG. 3 illustrates a graph of the stimulation of insulin secretion by-a glucose challenge in vitro.

Finally, in vitro functional studies demonstrate that islets cultured in the presence of IGF-I, NGF and insulin have a much improved insulin secretory response to a glucose challenge (the hallmark of β-cell function) (FIG. 3).

Figure 4:
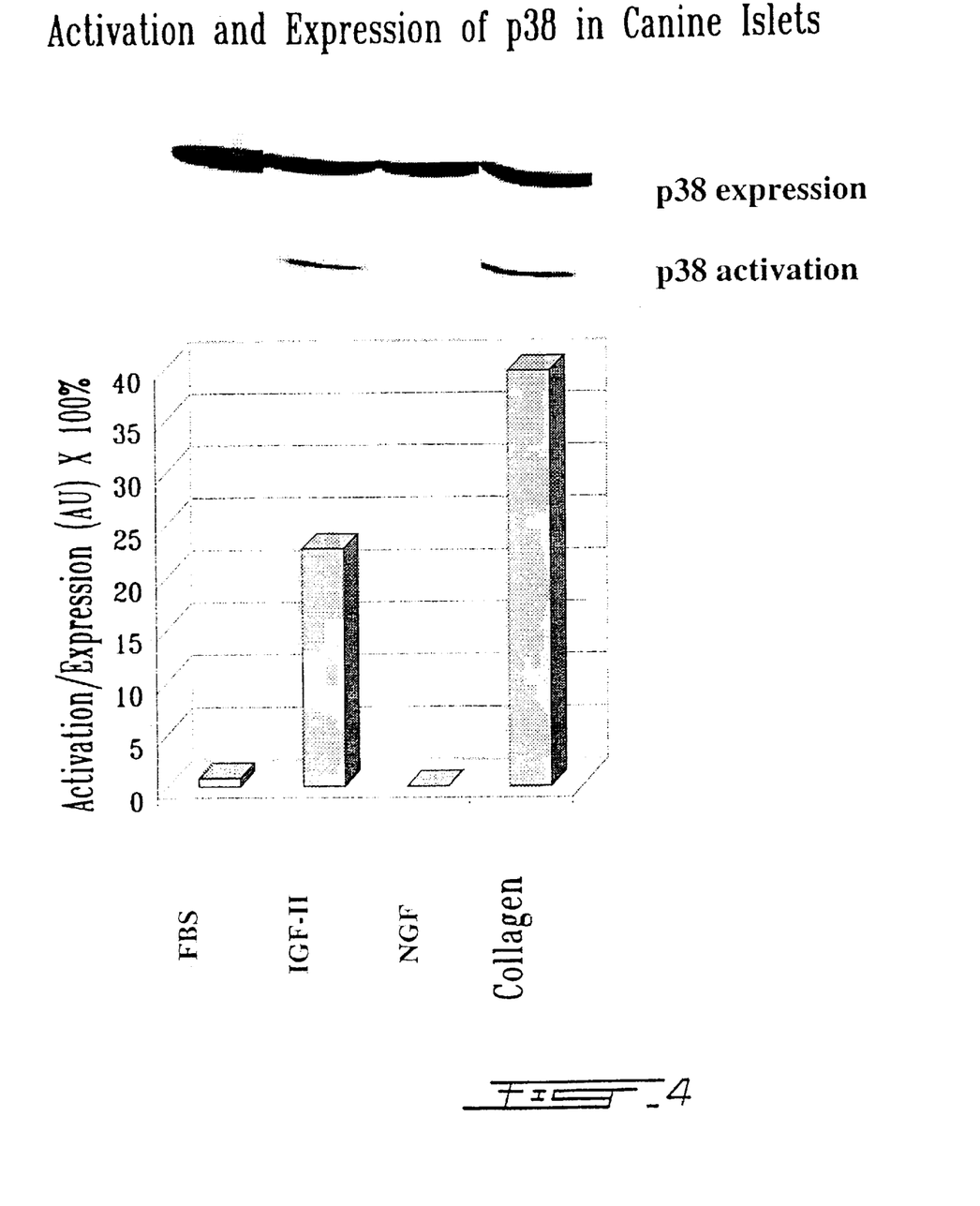
FIG. 4 illustrates activation and expression of p38 in canine islets.
Figure 5:
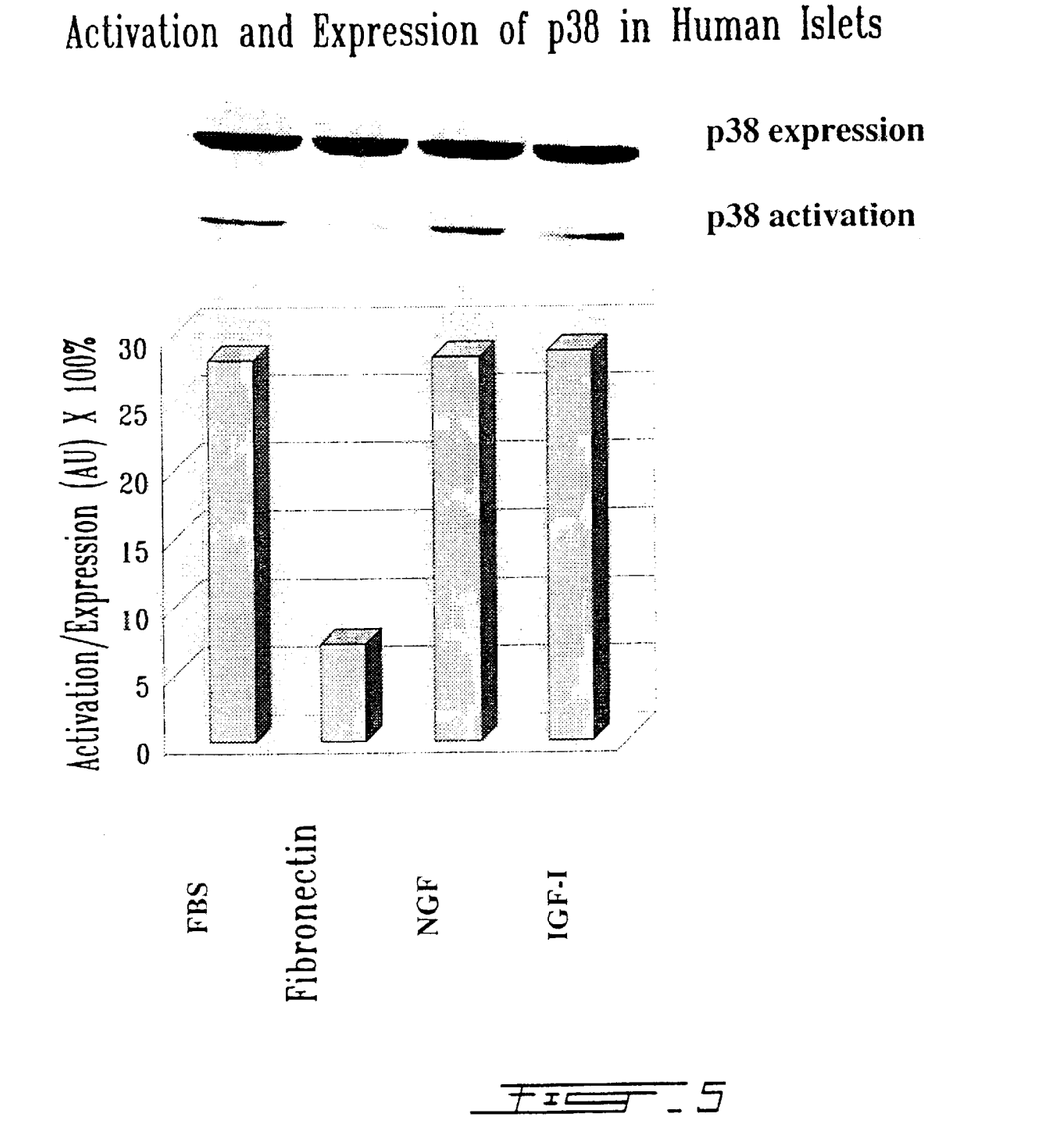
FIG. 5 illustrates-activation and expression of p38 in canine islets.

Signaling through the p38 MAP kinase is one pathway whose downstream effectors have been implicated in cell (FIGS. 4 and 5).

Suppression of p38 activation is necessary but not sufficient for the survival of islet cells (FIGS. 4 and 5).

Serum alone can suppress p38 activation, but it is not sufficient to enhance islet survival (FIGS. 4 and 5).

Trophic factor(s) (NGF, IGF-II) must be present to decrease islet cell death (see results presented in Example I which described the in vitro results of islet culture; FIG. 4). Not clearly seen on this graph, is the syneergism between IGF-II and NGF.

Depending on the state of p38 activation following islet isolation, growth factors can modulate the degree of activation. Conversely, since it is virtually impossible to assure uniformity of isolations if p38 (and associated signaling cascades) is activated as a result of a less than optimal isolation, subsequent intervention with the appropriate growth factors may not be effective. Therefore, these factors may need-to be provided "up front" during the digestion and purification phases, and not just during culture.

In addition to growth factors, evidence is provided for the beneficial effect of matrix molecules, e.g. fibronectin for human islets, and collagen for canine islets (FIGS. 4 and 5), The data for p38 activation and its modulation by collagen represents the effect of 200 µg/ml of collagen type 1. Not shown, is that collagen represents the effect of 200 µg/ml of collagen type 1. Not shown, is that collagen in a concentration of 400 µg/ml will decrease p38 activation by over 50%.

Signalling through erk has been associated with cell differentiation and cell survival (FIG. 6). These data, from human islet experiments, demonstrate that both insulin and IGF-I have a positive effect on erk1 and erk2 activation.

Figure 7:
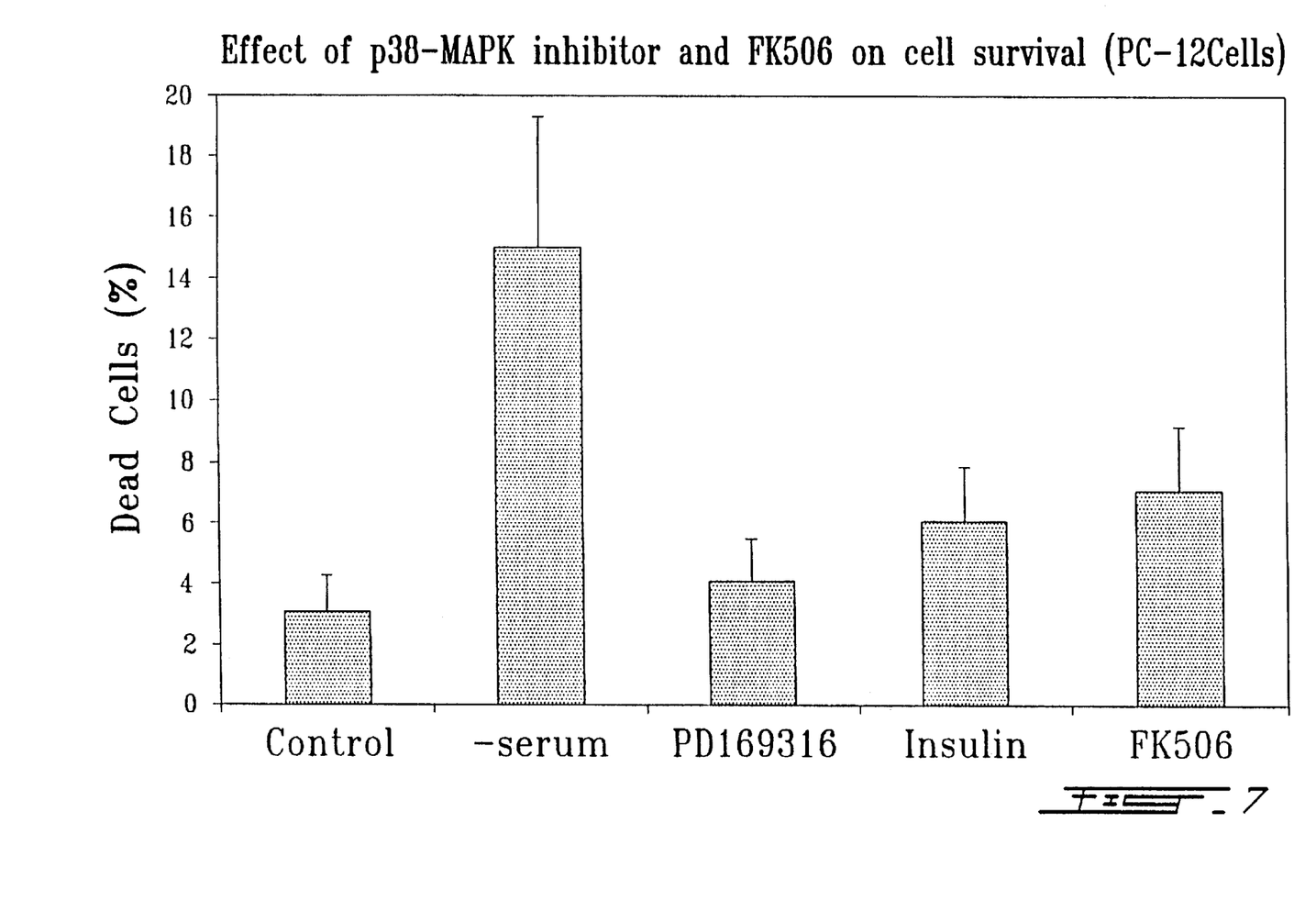
FIG. 7 illustrates the effect of p38-MAPK inhibitor and FK506 on cell survival (PC-12 cells)

NGF is the prototype of a family of neurotrophic factors that are important in the differentiation, maintenance and survival of neurons. Beta cells and neuronal cells share many characteristics and several markers initially thought to be specific for the nervous system have been found in beta cells. Of note, is the recent finding that beta cells express NGF receptors. The large number of similarities suggests that these two cell types could also share the same survival factors. PC-12 cells are a cell line of neuronal origin used for the above studies. FIG. 7 illustrates data from human islets which supports a similar role for FK506 and insulin islet survival. PD169316 is a specific p38 inhibitor.

The present invention will be more readily understood by referring to the following examples which are given to illustrate the invention rather than to limit its scope.

EXAMPLE I

Effect of Pancreatic Ductal Epithelium on Islet Cell Survival

In the present study, we extend our original observations to describe the influence of pancreatic duct epithelium on islet cell survival in vitro, and characterize for the first time the specific growth factors involved in an islet-duct paracrine interaction.

MATERIALS AND METHODS

Animals

Experiments were carried out with eight-week old female Syrian golden hamsters, 85 g body weight (Charles River, St. Jean, Quebec, Canada).

Experimental Design

Three experimental groups were designed for this study: Group 1 (control), with 100 islets per culture flask; Group 2 (islets plus ducts), with 100 islets plus 80 ducts per flask; and Group 3 (islets in 25% DCM), with 100 islets per flask.

All tissues were embedded in rat tail collagen and incubated in a humidified atmosphere of 95% air, 5% $CO_2$ at 37° C. The baseline medium for all groups was DMEM/F12, supplemented with 10% NuSerum for three days at the start of the culture period, followed by 9 days of serum-free incubation. The medium was changed every other day. A 12 day period was chosen because pilot studies had indicated that there was little change after this time.

Duct Isolation

The hamster pancreatic duct isolation was performed with collagenase XI solution (1 mg/ml) (Sigma, St. Louis, USA). Digestion was carried out in a stationary water bath at 37° C. for 30 minutes, followed by a 10 sec dispersion by vortex. After washing, the digest was filtered through a 94 µm steel mesh filter (Bellco Glass, Vineland, N.J., USA). The retained fragments were harvested by rinsing the inverted filter. The tissues were embedded into the neutralized rat tail collagen according to Richards (Richards et al., 1983, *Journal of Tissue Culture Methods* 8:31–36), and cultured in 2 ml of Dulbecco's modified Eagle medium/F12 (DMEM/F12) (Sigma, St. Louis, USA) supplemented with 10% NuSerum, insulin (1 g/ml, Eli Lilly, Toronto, Ontario, Canada), dexamethasone (1 g/L, Sigma, St. Louis, USA), soybean trypsin inhibitor (0.1 mg/ml, Gibco, Burlington, Ontario, Canada), cholera toxin (CT) (100 ng/ml, Sigma, St. Louis, USA), epidermal growth factor (EGF) (10 ng/ml, Sigma, St. Louis, USA), penicillin (100 U/ml, Gibco, Burlington, Ontario, Canada) and streptomycin (100 µg/ml, Gibco, Burlington, Ontario, Canada). After 10 to 12 days of culture, the collagen gel was dissolved by 0.25 mg/ml collagenase. Primary duct epithelial cysts were harvested, washed and re-embedded as before. This process was repeated twice to produce a culture of intralobular ductules by the 3rd week. The final tertiary duct culture was completely devoid of islets, acini and fibroblasts.

Duct-Conditioned Medium (DCM)

DCM was prepared from purified tertiary ducts incubated at 37° C. for three days in DMEM/F12 without NuSerum, CT, EGF, or insulin. The conditioned media was collected and stored at −80° C.

Islet Isolation

Islets were isolated from hamster pancreata according to a method previously established in our laboratory (Metrakos et al., 1993, *Surgery* 114:423–427; Metrakos et al., 1992, *Transplantation Proceedings* 24:2830–2831; Gray & Morris, 1987, *Transplantation* 43 321–331). In brief, 4 ml of collagenase P (Boehringer Mannheim, Laval, Canada) solution at 0.7 mg/ml was slowly introduced into the common bile duct after occlusion of the distal end just proximal to the duodenum. The distended pancreas was excised and the digestion was performed in a waterbath at 37° C. for 30 min. Islet purification was achieved using a two-step, discontinuous density gradient of bovine serum albumin (BSA) (Sigma, St. Louis, USA). Islets were collected from the interface between 1.000 and 1.081 g/ml layer. To ensure 100% purity of the preparation, islets were hand-picked and counted under an inverted microscope (Nikon TMS, Japan). The islets were recovered overnight in RPMI 1640 (Gibco, Burlington, Ontario, Canada) supplemented with 4% NuSerum (Collaborative Research Inc., Bedford, Mass., USA), penicillin (100 U/ml, Gibco) and streptomycin (100 µg/ml, Gibco).

Assessment of Cell Death

Microscopy

To calculate the number of islets with central necrosis in each experimental group, inverted light microscopy was used to monitor morphologic changes in the islets throughout the incubation period. The same tissue fields were photographed and counted at 1, 4, 6, 8 and 12 days. Necrosis at the center of an islet was characterized by a zone of very dark cells that was sharply demarcated from the surrounding viable islet tissue. The number of islets with central necrosis were counted and expressed as a percentage of the total. Islet size (µm) and the size of the area of necrosis were determined using a calibrated gradicule mounted in the eye-piece of the scope.

Histology

Culture dishes were sampled on days 1, 6, and 12. The tissue was fixed in 4% paraformaldehyde and embedded in paraffin. Serial sections (5µ thick and 50µ apart) were cut from each block, stained with haematoxylin and eosin (H&E) or toluidine blue, and then processed further for routine light microscopy.

Immunocytochemistry

Consecutive 5µ sections cut from the tissue block were immunostained for islet cell hormones (anti-human insulin antibody or rabbit polyclonal anti-glucagon or anti-somatostatin antibodies at a dilution of 1:100, Dako Corp., California), using the Streptavidin Biotin Complex method as described previously (Wang et al., 1997). The islet hormones are detected using NAMP/ Fast Red as chromagen to obtain a red reaction product. Negative controls are tissues processed with non-immune serum substituting for the 1° antibodies. To identify the presence of apoptotic cells, the tissues were co-processed for the TUNEL reaction (see below).

Detection of Apoptotic Cell Death

After a 12 day incubation period, the media was removed and 3 ml of collagenase XI (0.25 mg/ml) was added to each flask for 40 min. The islets were hand-picked and washed three times in Hank's buffered salt solution (HBSS, Gibco, Montreal, Quebec, Canada). The presence of DNA fragmentation, a characteristic feature of apoptosis was determined using a cell death detection ELISA (Boehringer Mannheim, Laval, Quebec). The results were expressed as absorbance at 405 nm and corrected for total DNA content. DNA (µg) was measured by fluorometry using disbenzimidazole (Hoechst 33258, Sigma, Montreal, Quebec) as described (Labarca & Pagen, 1987, *Analytical Biochemistry* 102:44–52).

To identify which cells in the islet were undergoing apoptosis, a TUNEL was employed. Islets were fixed in 4% paraformaldehyde and embedded in paraffin. 5 µm paraffin sections were cut and pretreated with 0.1% Trypsin buffer in 37° for 5 min. The In Situ Cell Death Detection Kit (Boehringer Mannheim, Laval, Quebec) was used for the labeling of apoptotic cells and the sections were developed with DAB (Sigma, St Louis, Mo.). To reduce non-specific labeling the POD antibody conjugate was diluted 1:5 in TBS buffer. Approximately 800 cells from 10 islets were counted in each group, and an apoptotic index (% of labeled cells) was calculated.

Analysis of Culture Medium for Growth Factors

Samples of duct conditioned culture medium were subjected to acid gel chromatography on Sephadex G50 to separate insulin-like growth factor binding proteins prior to performing specific radioimmunoassays for IGFI and IGF-II. These assays were carried as described by Hill (Hill, 1990, *Early Human Development* 21:49–58).

Analysis of the effect of IGF-II

The islets were embedded in rat tail collagen and cultured in DMEM/F12 supplemented with 10% NuSerum. After three days in culture, three experimental groups were designed for this study: Group 1 (control), islets cultured in DMEM/F12; Group 2, islets cultured in DMEM/F12+ 25%DCM; and Group 3, islets cultured in DMEM/F12+34 ng/ml IGF-II. The islets were retrieved from the collagen following 9 days in culture with this media.

Statistical Analysis

The results obtained for all culture dishes within a group were pooled, and expressed as mean±SEM (n=number of culture dishes). The differences between the three experimental groups with respect to the presence of central necrosis, cytoplasmic DNA fragmentation, and the apoptotic index, were analyzed by unpaired Student's t-test. The relationship between islet size and the presence or absence of central necrosis, and the relationship between islet size and the size of the area of necrosis was determined by Chi-square analysis. Except for the IGF-II apoptosis study, all experiments were performed twice and the results were averaged. P-values less than 0.05 were considered statistically significant.

RESULTS

Characteristics of Islets and Ducts Following Isolation

The average number of islets isolated was 475±108 per pancreas. Immediately after isolation, islet purity, as determined by dithazone staining, ranged from 80 to 95%, but this reached nearly 100% on the second day following the final transfer of islets onto the culture dishes. Islet diameter ranged from 50 to 300 μm, with the majority measuring 100 to 200 μm. Under the inverted microscope, freshly isolated islets had a smooth appearance with slightly irregular borders. After overnight incubation, the islets recovered a more regular spherical shape with well defined smooth borders.

At the start of the study, the mean islet diameter (μm) was similar in each of the three treatment groups—islets alone (161±34 μm) vs. islets+ducts (164±61 μm) vs. islets+DCM (155±51 μm).

More than 2000 duct epithelial cysts were isolated per gm of pancreatic tissue. Following two passages, cultures of pure duct epithelial cysts were obtained, with the lining wall composed of a single layer of cubical or flattened epithelium.

Analysis of Morphological Changes

Examination of islets on day 1 demonstrated normal morphology in each group. The islet cells were compact, regularly shaped, with well defined nuclei and a grainy appearance of the cytoplasm. There was no evidence of central necrosis in any of the groups on the first day of culture.

By day 3, however, a central area of very dark tissue with borders sharply demarcating the surrounding islet cells became visible under the inverted microscope. This same area observed by routine histology was seen to be composed of necrotic cells in the islet core, and by day 6, extensive areas of necrotic cells in the central islet region were apparent. Once established, the zone of necrosis persisted for the duration of the incubation period and even increased in size.

Figure 8:
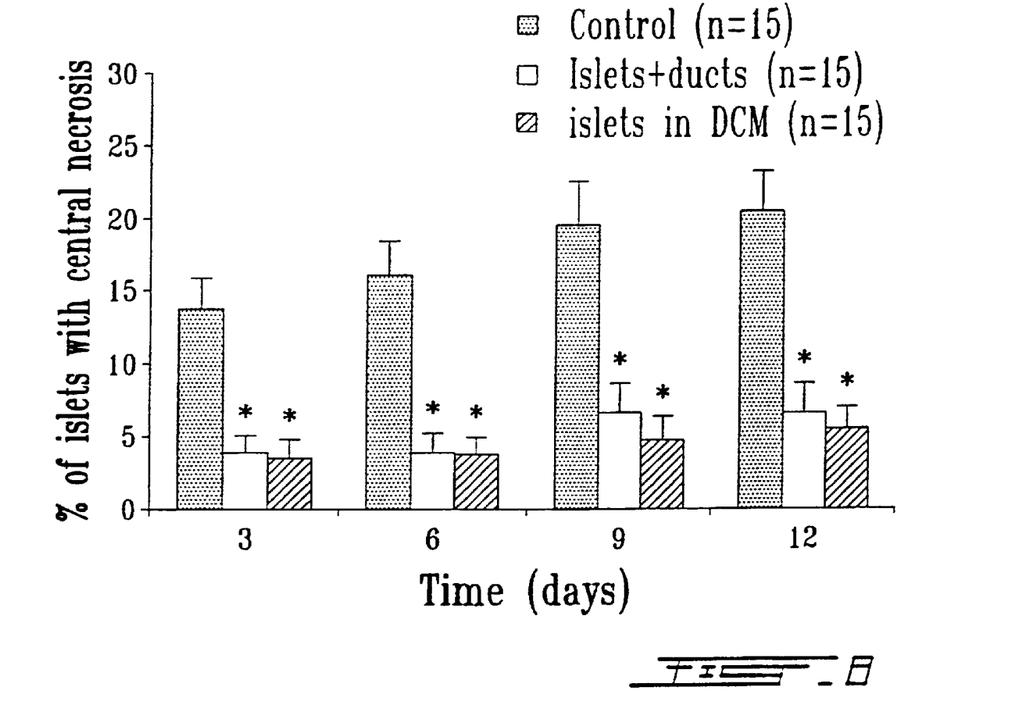
FIG. 8 illustrates the effect of ductal epithelium and duct-conditioned medium on islet necrosis development.

Islets cultured alone had a significant increase in central necrosis ($p<0.001$) at all time points when compared to islets in the other two groups (FIG. 8). Data are mean±SEM, (n=15). * $P<0.001$ (Student's t test). By day 12, 20.6±3% of the islets cultured alone were necrotic, compared to 6.7±2% of the islets cocultured with ducts and 5.6±1.5% of the islets cultured in DCM respectively. There was no difference between islets in the duct co-culture and DCM groups.

The presence or absence of central necrosis was associated with islet size ($p<0.01$), with the area of necrosis being greatest in islets larger than 150 μm. Half way through the study period, there as no significant difference in the mean diameter (μm) of islets with central necrosis whether they were cultured alone (192±49 μm), co-cultured with ducts (209±46 μm), or cultured with DCM (187±42 μm).

Analysis of Cell Survival

Figure 9:
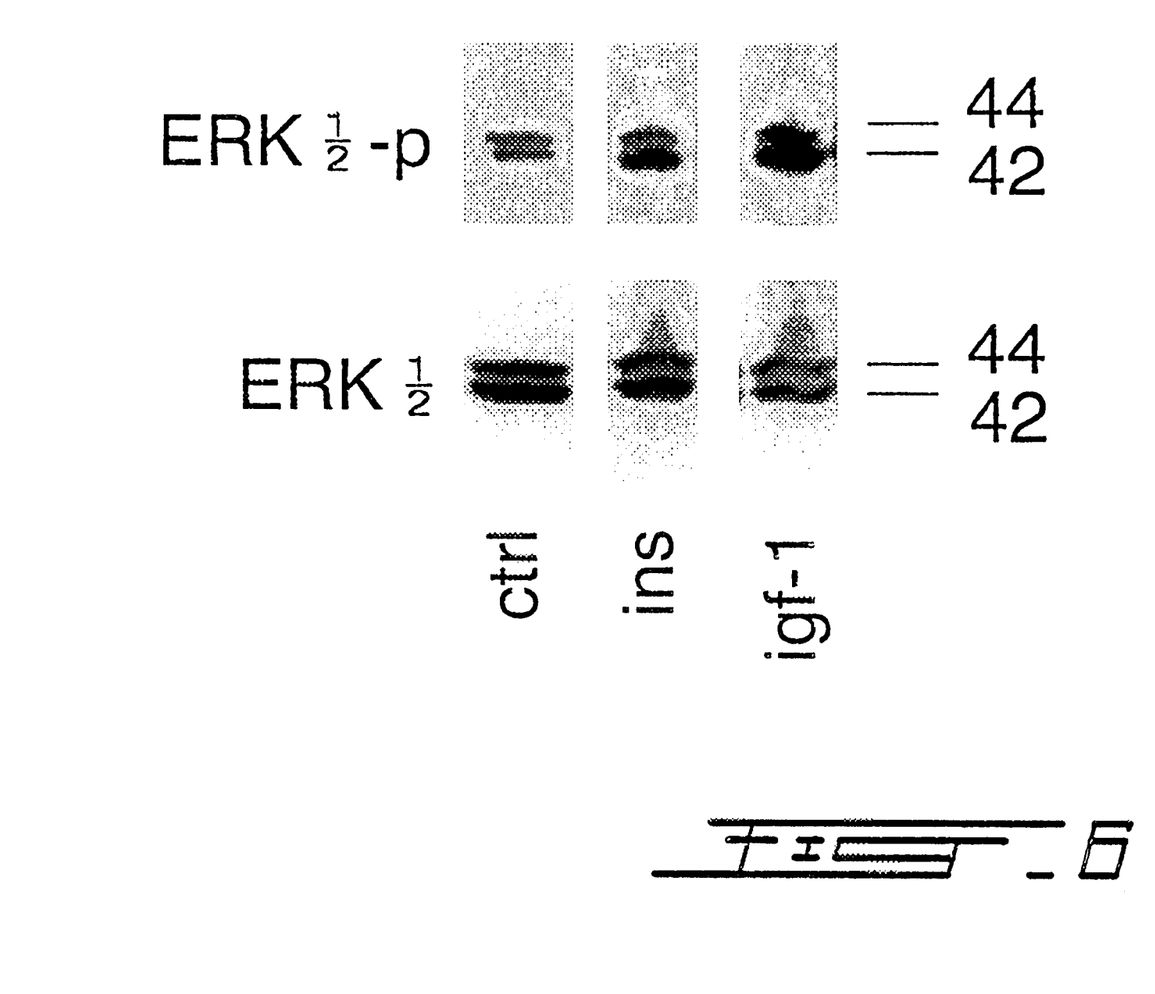
FIG. 9 illustrates the effect of ductal epithelium and duct-conditioned medium on DNA fragmentation.

After 12 days of culture, islets in the duct coculture and DCM groups showed less evidence of apoptosis compared to islets cultured alone. Using the cell death ELISA, the cytoplasmic nucleosome content of islets cultured alone was increased significantly when compared to islets co-cultured with ducts or islets cultured in medium supplemented with DCM (2.3±0.2 versus 0.9±0.5 and 1.1±0.8; $p<0.05$) (FIG. 9). Data are mean+SEM (n=8). * P=0.03 Islets+duct vs. Islets (Student's t test); † P=0.04 Islets in DCM vs. Islets (Student's t test). The apoptotic index (% TUNEL positive cells) demonstrated a significant difference ($p<0.001$) between islets cultured alone (60.8±3.9%) compared to those co-cultured with ducts (29.8±8.3%) or in DCM supplemented medium (38.3±1.5%). Over 80% of TUNEL-positive cells were in the inner 80% of the islet, suggesting that these were primarily beta cells. Double labeling of cells for islet cell hormones confirmed this impression, although as anticipated, many TUNEL-positive cells in fact did not show immunoreactivity for any islet cell hormone.

Analysis of Duct Conditioned Medium and the Effect of IGF-II

After completion of this initial series of studies, duct conditioned medium was analyzed for growth factors that might be expected to be secretory products of pancreatic ductal epithelium, based on previous literature reports. Our analysis demonstrated the presence of a small amount NGF (4 ng/ml) and much larger amount of IGF-II (34 ng/ml). IGF-I was not identified.

Figure 10:
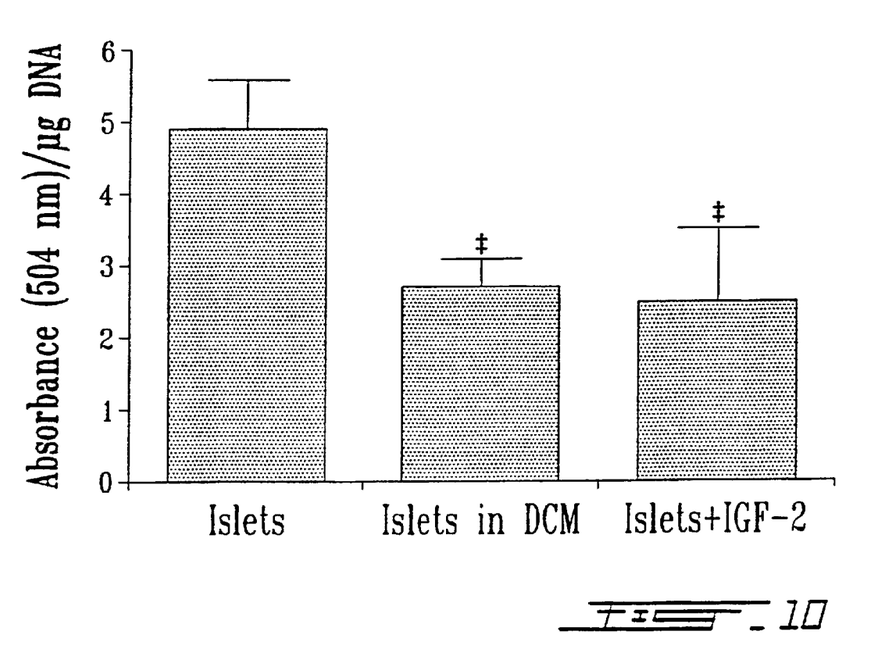
FIG. 10 illustrates the effect of ductconditioned medium and IGF-II on DNA fragmentation.

The culture studies were then repeated to compare the outcome by cell death ELISA, for islets cultured alone, to islets+DCM and islets+IGF-II. The results demonstrated that IGF-II could account for the beneficial effect of DCM ($p<0.004$) with respect to limiting apoptosis in cultured islets (islet alone-4.9±0.7; islets+DCM-2.7±0.4; islets+IGF-2.5+1.0; FIG. 10). Data are mean±SEM (n=6) ‡ $P<0.004$ (Student's t test).

When maintained under standard in vitro conditions, islet cells, predominantly in the islet core, underwent necrotic cell death. This finding is in keeping with a number of previous studies that have also documented the occurrence of central necrosis in islets maintained in vitro. In the present study, however, when islets were co-localized with duct epithelium or with the secretory products of duct cells, the occurrence of central islet necrosis was diminished significantly.

In the present study, after 12 days of incubation, purified islets sustained a significant increase in apoptotic cell death compared to islets cocultured with duct cells or those maintained in medium supplemented with DCM. This finding is consistent with the suggestion that islet isolation and purification may trigger apoptosis by removing important trophic factors responsible for the maintenance of islet cell viability. It remains to be established, however, whether both types of cell death, necrosis and apoptosis, are induced coincidentally by the same set of circumstances, i.e., the withdrawal of trophic factors and the environmental conditions to which the islets are exposed.

We conclude that pancreatic ductal epithelium promotes islet cell survival. This effect appears to be mediated in a paracrine manner by the release of IGF-II from cells in the ductal epithelium.

EXAMPLE II

Synergistic Anti-apoptotic Effect of IGF-I and FK-506

Figure 11:
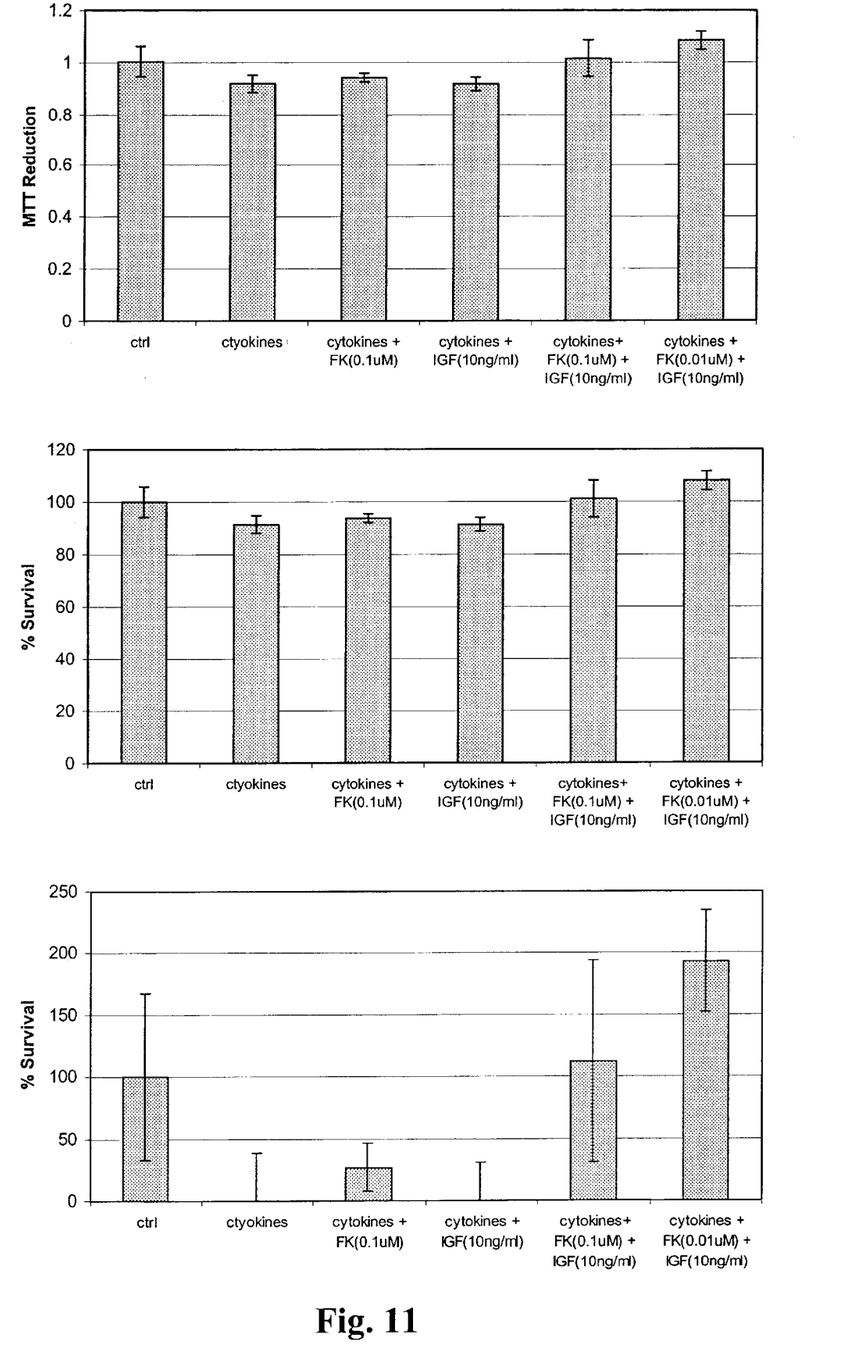
FIG. 11 illustrates the synergistic antiapoptotic effect of FK-506 in combination with IGF-I on islet cells.

Isolated canine islets were cultured for 48 h in medium CMRL 1066 containing 10% FBS. Following 6 h of serum withdrawal, islets were pretreated for 30 minutes with FK506 (FK) and/or IGF-I, and then treated with cytokines (IL-1β, 100 U/ml, TNF-α, 100 ng/ml and INFγ, 100 ng/ml) for 48 h. Survival was assessed by MTT reduction assay as shown in FIG. 11. Bars represent means+/−S.E. (n=4).

Figure 12:
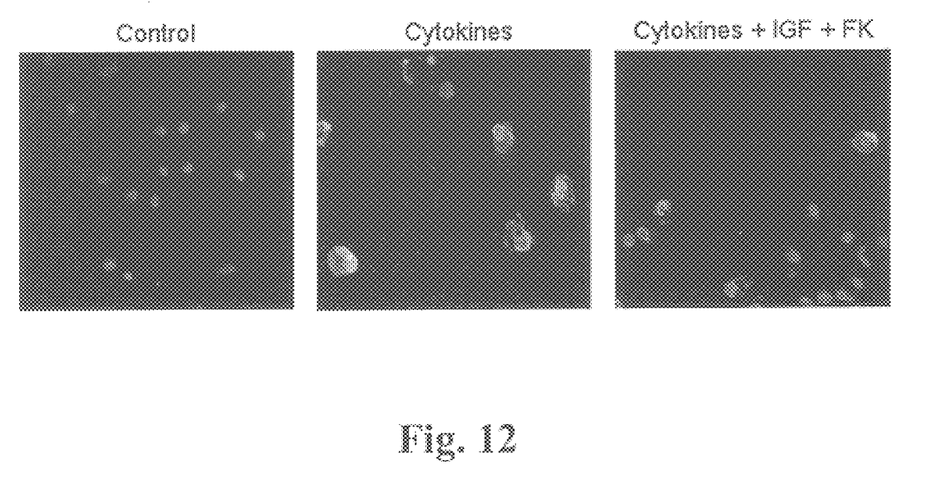
FIG. 12 illustrates the synergistic antiapoptotic effect of FK-506 in combination with IGF on islet cells.

Canine islets were recovered overnight in serumcontaining CMRL 1066. Following 4 h of serum withdrawal, the islets were pretreated with IGF and/or FK for 30 minutes and then subsequently treated with a cytokine mixture for 48 h. Survival was assed by Annexin-V/PI staining as shown in FIG. 12. The nuclei of both dead and alive cells was stained red using a high concentration of PI (10 μM). Apoptotic and necrotic cells were stained green. The IGF/FK treatment was able to reduce the amount of cell death caused by the cytokine stimulus.

Figure 13:
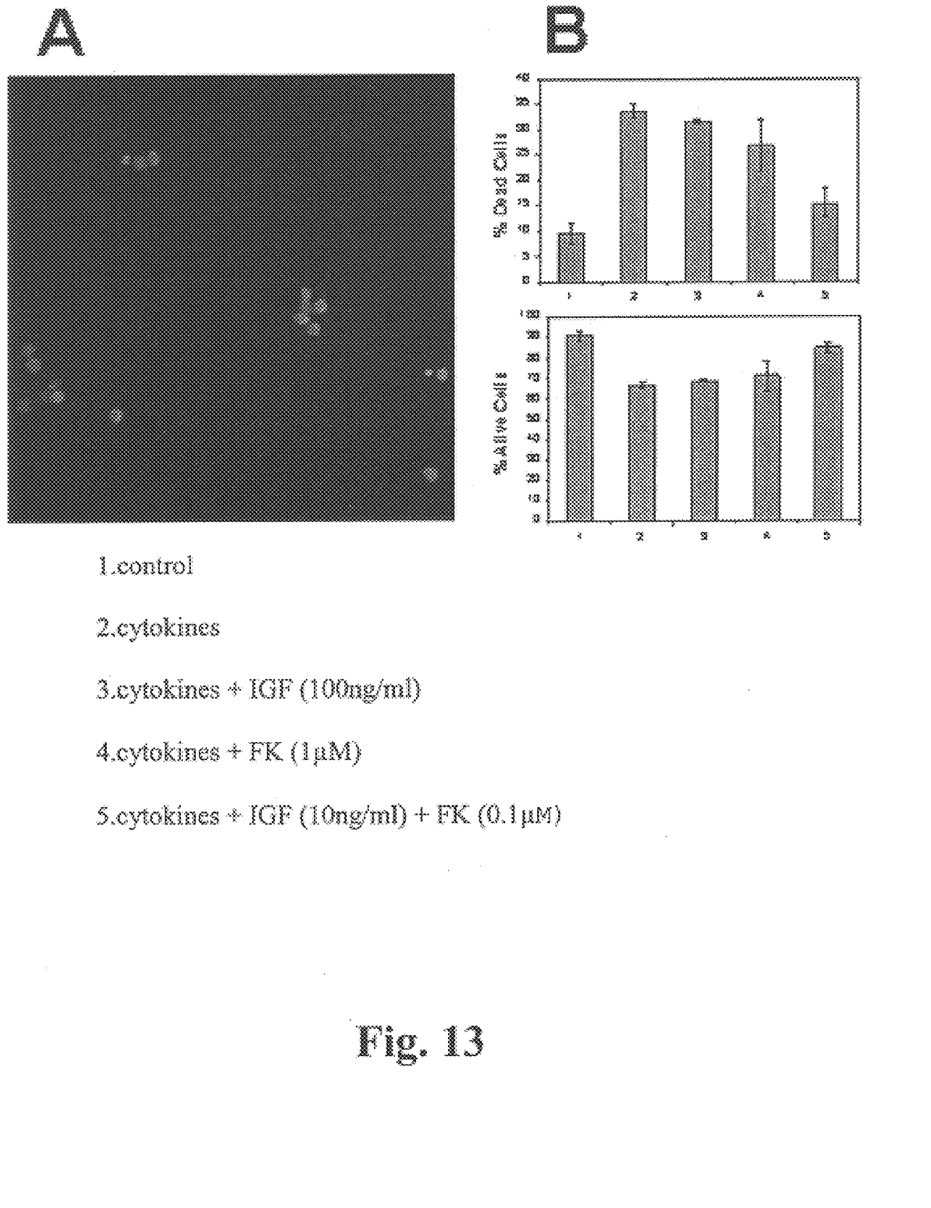
FIGS. 13A–B illustrate the synergistic anti-apoptotic effect of FK-506 in combination with IGF on islet cells.

Canine islets were recovered overnight in serumcontaining CMRL 1066. Following 4 h of serum withdrawal, the islets were pretreated with IGF and/or FK for 30 minutes and then subsequently treated with a cytokine mixture for 24 h. Survival was assed by counting PI/FDA stained cells from dispersed islets. FDA positive cells (green) were alive (FIG. 13A), while the PI positive cells (red) were dead (FIG. 13B). The dead and alive cells were expressed as a percentage of the total cells counted (500 cells in triplicate for each group). Bars represent means+/−S.E. (n=3).

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

What is claimed is:

1. A medium for promoting the survival of islet cells, which comprises one or more growth factors in combination with FK506 in amounts having an antiapoptotic apoptotic effect on islet cells in a physiologically acceptable culture medium.

2. The medium of claim 1, wherein said growth factor is selected from the group consisting of NGF, IGF-I and IGF-II.

3. The medium of claim 2, wherein NGF is in a concentration of from about 10 to about 100 ng/ml of medium and IGF-I or IGF-II is in a concentration of from about 10 to about 100 ng/ml of said medium.

4. The medium of claim 1, which further comprises an immunosuppressant.

5. The medium of claim 1, wherein said FK506 is in a concentration of about 1 micromolar.

6. The medium of claim 1, which further comprises insulin.

7. The medium of claim 5, which comprises insulin at a concentration of from about 10 to about 100 ng/ml of medium.

8. The medium of claim 7, wherein said physiologically acceptable culture medium is selected from the group consisting of CMRL 1066, RPMI 1640 and DMEM/F12.

9. The medium of claim 1, wherein said growth factor is obtained from primary duct cultures that have been passaged to remove cellular elements other than duct cells.

10. The medium of claim 1, which further comprises a soluble matrix molecule.

11. The medium of claim 10, wherein said soluble matrix molecule is fibronectin or collagen.

12. A method for maintaining viability of islet cells, which comprises contacting said islet cells with a medium according to claim 1.

13. The method of claim 12, wherein said contacting is effected by isolating said islet cells or by irrigating said islet cells at a site of transplant.

14. A method for producing a medium promoting islet cell survival, which comprises:

a) preparing a tertiary pancreatic duct culture from primary duct epithelial islets; and b) purifying the prepared tertiary pancreatic duct culture and incubating the purified culture in a physiologically suitable medium containing one or more growth factors in combination with FK506 in an amount effective for maintaining viability of said islet cells when in contact therewith.

15. The method of claim 14, wherein maintaining viability of said islet cells is effected by inhibiting induction of apoptosis in said islet cells.

16. A method for maintaining viability of islet cells, which comprises contacting said islet cells with a medium according to claim 11.

17. A medium for promoting the survival of islet cells comprising, in a physiologically culture medium, IGF-I or IGF-II in combination with NGF in an amount having a synergistic anti-apoptotic effect on islet cells.

18. The medium of claim 17, further comprising FK506.

19. The medium of claim 18, wherein said FK506 is in a concentration of about 1 micromolar.

20. The medium of claim 19, wherein NGF is in a concentration of from about 10 to about 100 ng/ml of medium and IGF-I or IGF-II is in a concentration of from about 10 to about 100 ng/ml of said medium.

21. The medium of claim 17, which further comprises an immunosuppressant.

22. The medium of claim 17, which further comprises insulin.

23. The medium of claim 22, which comprises insulin at a concentration of from about 10 to about 100 ng/ml of medium.

24. The medium of claim 23, wherein said physiologically acceptable culture medium is selected from the group consisting of CMRL 1066, RPMI 1640 and DMEM/F12.

25. The medium of claim 17, wherein said growth factor is obtained from primary duct cultures that have been passaged to remove cellular elements other than duct cells.

26. The medium of claim 24, which further comprises a soluble matrix-molecule.

27. The medium of claim 26, wherein said soluble matrix molecule is fibronectin or collagen.

* * * * *